US010591448B2

(12) United States Patent
Astarita

(10) Patent No.: US 10,591,448 B2
(45) Date of Patent: Mar. 17, 2020

(54) STRUCTURAL ELUCIDATION OF ISOTOPICALLY LABELED ANALYTES

(71) Applicant: Waters Technologies Corporation, Milford, MA (US)

(72) Inventor: Giuseppe Astarita, Hopkinton, MA (US)

(73) Assignee: Waters Technologies Corporation, Milford, MA (US)

(*) Notice: Subject to any disclaimer, the term of this patent is extended or adjusted under 35 U.S.C. 154(b) by 0 days.

(21) Appl. No.: 15/566,587

(22) PCT Filed: Apr. 14, 2016

(86) PCT No.: PCT/US2016/027409
§ 371 (c)(1),
(2) Date: Oct. 13, 2017

(87) PCT Pub. No.: WO2016/168391
PCT Pub. Date: Oct. 20, 2016

(65) Prior Publication Data
US 2018/0143169 A1 May 24, 2018

Related U.S. Application Data

(60) Provisional application No. 62/147,216, filed on Apr. 14, 2015.

(51) Int. Cl.
H01J 49/00 (2006.01)
G01N 33/50 (2006.01)
(Continued)

(52) U.S. Cl.
CPC ............. G01N 30/72 (2013.01); G01N 33/50 (2013.01); G01N 33/5038 (2013.01);
(Continued)

(58) Field of Classification Search
CPC .... G01N 30/72; G01N 33/50; G01N 33/5038; G01N 33/6848; H01J 49/0036; H01J 49/0045; H01J 49/40
See application file for complete search history.

(56) References Cited

U.S. PATENT DOCUMENTS 6,586,727 B2 7/2003 Bateman et al.
6,717,130 B2 4/2004 Bateman et al.
(Continued)

FOREIGN PATENT DOCUMENTS

EP 1385194 A2 1/2004
GB 2363249 A 12/2001
(Continued)

OTHER PUBLICATIONS

International Search Report and Written Opinion for International Application No. PCT/US2016/027409, dated Jun. 14, 2016 and dated Jul. 15, 2016.
(Continued)

Primary Examiner — Nicole M Ippolito
Assistant Examiner — Sean M Luck
(74) Attorney, Agent, or Firm — Womble Bond Dickinson (US) LLP; Deborah M. Vernon; Benedict L. Hanrahan

(57) ABSTRACT

The present disclosure relates to structural elucidation of isotopically labeled analytes using chromatography-MS and data-independent acquisition. The present disclosure can be used for rapid screening of analytes, such as the metabolome, including the simultaneous collection of both qualitative and quantitative information of known and unknown analytes.

13 Claims, 5 Drawing Sheets

(51) Int. Cl.
*H01J 49/40* (2006.01)
*G01N 30/72* (2006.01)
*G01N 33/68* (2006.01)

(52) U.S. Cl.
CPC ...... *G01N 33/6848* (2013.01); *H01J 49/0036* (2013.01); *H01J 49/0045* (2013.01); *H01J 49/40* (2013.01); *G01N 2458/15* (2013.01); *G01N 2560/00* (2013.01)

(56) References Cited

U.S. PATENT DOCUMENTS

| | | | |
|---|---|---|---|
| 7,820,964 | B2 | 10/2010 | Beecher |
| 2003/0180710 | A1 | 9/2003 | Lee et al. |
| 2006/0121618 | A1* | 6/2006 | Shilov ................ G01N 33/6842 436/86 |
| 2007/0278395 | A1 | 12/2007 | Gorenstein et al. |
| 2008/0050833 | A1 | 2/2008 | Smith et al. |
| 2008/0070314 | A1* | 3/2008 | Geromanos ........ G01N 33/6848 436/86 |
| 2008/0272292 | A1 | 11/2008 | Geromanos et al. |
| 2010/0301205 | A1* | 12/2010 | Thomson ............ H01J 49/0027 250/283 |
| 2012/0156712 | A1 | 6/2012 | Takats |
| 2012/0165227 | A1 | 6/2012 | Li et al. |
| 2012/0282641 | A1* | 11/2012 | Reilly ................ G01N 33/6818 435/23 |
| 2013/0206979 | A1* | 8/2013 | Bonner ............... H01J 49/0031 250/282 |
| 2014/0199716 | A1* | 7/2014 | Bertozzi ............ G01N 33/6848 435/23 |
| 2014/0346345 | A1* | 11/2014 | Makarov ............ H01J 49/0031 250/283 |
| 2015/0028199 | A1 | 1/2015 | Geromanos et al. |

FOREIGN PATENT DOCUMENTS

| | | |
|---|---|---|
| WO | 2005/114930 A2 | 12/2005 |
| WO | 2009/021056 A1 | 2/2009 |
| WO | 2016/196181 A1 | 12/2016 |

OTHER PUBLICATIONS

Extended European Search Report relating to European Application No. 16780697.5 dated Sep. 28, 2018.

Jong et al., "Addressing the current bottlenecks of metabolomics: Isotopic ratio outlier analysis, an isotopic-labeling technique for accurate biochemical profiling," Bioanalysis, Sep. 2012, 4(18), 2303-2314.

Mahieu et al., "Credentialing features: A platform to benchmark and optimize untargeted metabolomics methods," Anal. Chem. 2014, 86, 9583-9589.

Stupp et al., "Isotopic ratio outlier analysis global metabolomics of Caenorhabditis elegans," Anal. Chem. 2013, 85, 11858-11865.

Thou et al., "IsoMS: Automated processing of LC-MS data generated by a chemical isotope labeling metabolomics platform," Anal. Chem. 2014. 86, 4675-4679.

* cited by examiner

STRUCTURAL ELUCIDATION OF ISOTOPICALLY LABELED ANALYTES

CROSS REFERENCE TO RELATED APPLICATIONS

This application is a National Stage Application of International Application No. PCT/US2016/027409 filed Apr. 14, 2016, which claims benefit of and priority to U.S. Provisional Application No. 62/147,216 filed Apr. 14, 2015, the content of each of which is incorporated herein by reference in its entirety.

FIELD OF THE TECHNOLOGY

The present disclosure relates to structural elucidation of isotopically labeled analytes using chromatography, mass spectrometry and data-independent acquisition. The present disclosure can be used for rapid screening, such as for the metabolome, including the simultaneous collection of both qualitative and quantitative information of known and unknown analytes.

BACKGROUND OF THE INVENTION

Analyte identification is difficult in complex biological samples which may contain numerous different analytes. For instance, metabolite identification is a bottleneck of most metabolomics studies. Common analysis techniques used with complex biological samples often include a separation step, such as chromatography, followed by a quantitative and/or qualitative detection step, such as mass spectrometry. Yet, in complex samples many of the analytes co-elute at the same retention time and/or appear in similar regions of the mass/charge (m/z) scale making determinations difficult. Additionally, the presence of noise signals, impurities associated with sample collection or extraction procedures, etc. and the presence of other non-biological related material can also interfere with the analysis.

The use of stable-isotope assisted methods, including labeling and internal standard approaches, can mitigate some of these difficulties. See Jong et al., "Addressing the current bottlenecks of metabolomics: Isotopic ratio outlier analysis, an isotopic-labeling technique for accurate biochemical profiling," Bioanalysis, 2012 September, 4(18), 2303-2314; Stugg et al., "Isotopic ratio outlier analysis global metabolomics of *Caenorhabditis elegans*," Anal. Chem. 2013, 85, 11858-11865; Zhou et al., "IsoMS: Automated processing of LC-MS data generated by a chemical isotope labeling metabolomics platform," Anal. Chem. 2014. 86, 4675-4679; and Mahieu et al., "Credentialing features: A platform to benchmark and optimize untargeted metabolomics methods," Anal. Chem. 2014, 86, 9583-9589, each of these references are incorporated by reference herein in their entirety. In simple situations, such as where the biological relevant analytes have been identified or are known, the characterization of their structure often relies only on accurate mass and isotopic pattern. In complex samples, the characterization is more challenging. These stable-isotope assisted methods used in conjunction with MS information or data dependent acquisition provide limited ability to overcome these challenges and provide robust structural elucidation. Additional techniques and methodology is needed for rapid and robust quantification and qualification of complex samples.

SUMMARY OF THE INVENTION

The present disclosure relates to structural elucidation of isotopically labeled analytes using chromatography, mass spectrometry and data-independent acquisition. For example, the present disclosure can be used for structural elucidation of the metabolome using various stable-isotope assisted methods, such as isotopic ratio outlier analysis, in combination with chromatography-MS, such as ultra high performance liquid chromatography-quadrupole time of flight mass spectrometry (UHPLC-QTOF), and data-independent acquisition.

In one embodiment, the present disclosure relates to a method including receiving a high energy fragmentation mass spectrum and a low energy fragmentation mass spectrum of a ion, identifying at least one characteristic set of peaks in the low energy fragmentation mass spectrum, identifying at least one characteristic set of peaks in the high energy fragmentation mass spectrum that are substantially similar to the characteristic set of peaks in the low energy fragmentation mass spectrum, and determining a chemical structure of the ion from the combination of at least one characteristic set of peaks in the high energy fragmentation mass and the at least one characteristic set of peaks in the low energy fragmentation mass. The high energy fragmentation mass spectrum and the low energy fragmentation mass spectrum can be generated using the compositions and methods of the present disclosure, such as a quadrupole time of flight mass spectrometer operating in data independent mode. The high and low energy fragmentation mass spectra can be generated at substantially the same time. For example, the spectra can be generated during the analysis of real time data as required when the source of the ions is the eluent from a chromatography device.

In another embodiment, the present disclosure relates to a method including providing an ion source for generating ions, passing said ions to a fragmentation means including a collision cell, operating said fragmentation means in a first mode wherein at least a portion of said ions are fragmented to produce daughter ions, recording a mass spectrum of ions emerging from said fragmentation means operating in said first mode as a high energy fragmentation mass spectrum, switching said fragmentation means to operate in a second mode wherein substantially fewer ions are fragmented, recording a mass spectrum of ions emerging from said fragmentation means operating in said second mode as a low energy fragmentation mass spectrum, repeating these steps a plurality of times, identifying at least one characteristic set of peaks in the low energy fragmentation mass spectrum, identifying at least one characteristic set of peaks in the high energy fragmentation mass spectrum that is substantially similar to the characteristic set of peaks in the low energy fragmentation mass spectrum, and determining a chemical structure associated with the at least one characteristic set of peaks in the high energy fragmentation mass and the at least one characteristic set of peaks in the low energy fragmentation mass. In some embodiments, the method can include providing an ion source for generating ions.

The characteristic set of peaks in the high energy fragmentation mass spectrum can have substantially the same number of peaks, substantially the same spacing between any two or more peaks, substantially the same intensity ratio between any two or more peaks as the characteristic set of peaks in the low energy fragmentation mass spectrum or combinations thereof.

In another embodiment, the present disclosure relates to a mass spectrometer having an ion source for generating ions, a fragmentation means switchable between at least a high energy mode in which at least portion of the ions received by the fragmentation means are fragmented to produce daughter ions and a low energy mode in which substantially fewer of the ions are fragmented than in high energy mode, and a mass analyzer for mass analyzing at least some of the ions which have passed through the fragmentation means operating in the high energy mode and for mass analyzing at least some of the ions which have passed through the fragmentation means operating in the low energy mode, wherein the mass spectrometer is configured to identify at least one characteristic set of peaks in the low energy fragmentation mass spectrum and to identify at least one characteristic set of peaks in the high energy fragmentation mass spectrum that is substantially similar to the characteristic set of peaks in the low energy fragmentation mass spectrum. In exemplary embodiments, a voltage greater than or equal to about 15V can applied to the fragmentation means in the high energy mode. In exemplary embodiments, a voltage less than or equal to about 10V can be applied to the fragmentation means in the low energy mode.

The mass spectrometer can have a control system, wherein the control system can be arranged to identify at least one characteristic set of peaks in the low energy fragmentation mass spectrum, identify at least one characteristic set of peaks in the high energy fragmentation mass spectrum that is substantially similar to the characteristic set of peaks in the low energy fragmentation mass spectrum. The mass spectrometer can also be configured to determine a chemical structure associated with the at least one characteristic set of peaks in the high energy fragmentation mass and the at least one characteristic set of peaks in the low energy fragmentation mass. The mass spectrometer can have a data processor, software, or similar wherein the data processor or software can be arranged to determine a chemical structure associated with the at least one characteristic set of peaks in the high energy fragmentation mass and the at least one characteristic set of peaks in the low energy fragmentation mass.

The present disclosure provides a number of advantages over current methods and apparatus. For example, the application of chromatography and data-independent acquisition (e.g., LC-DIA) to metabolite extracts from biological samples often results in MS/MS spectra containing a mixture of product ions derived from multiple, co-eluting precursors, complicating interpretation of the spectra and the overall identification process. By combining stable-isotope assisted method and a chromatography-MS technique with data-independent acquisition allows both qualitative and quantitative assessment of the complex mixture to determine the structure of one or more of the analytes.

BRIEF DESCRIPTION OF THE DRAWINGS

The foregoing and other features and advantages provided by the present disclosure will be more fully understood from the following description of exemplary embodiments when read together with the accompanying drawings, in which.

DETAILED DESCRIPTION OF THE INVENTION

Figure 1:
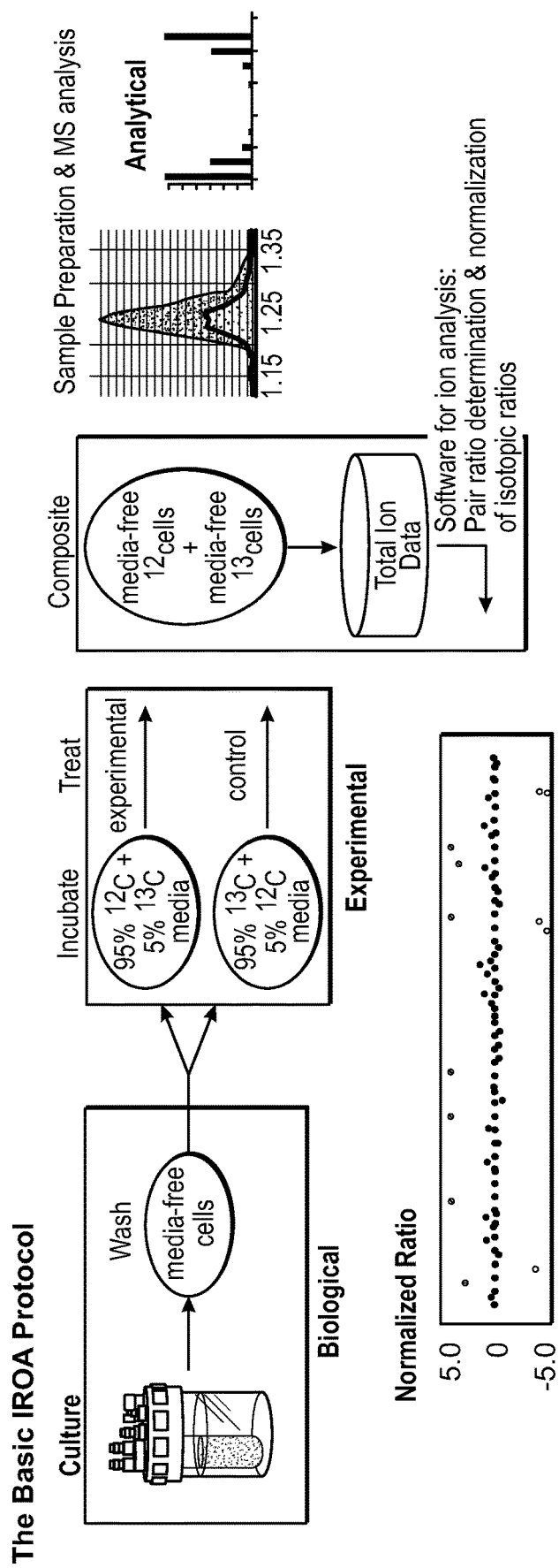
FIG. 1 shows an exemplary schematic of the basic isotopic ratio outlier analysis.
Figure 1:
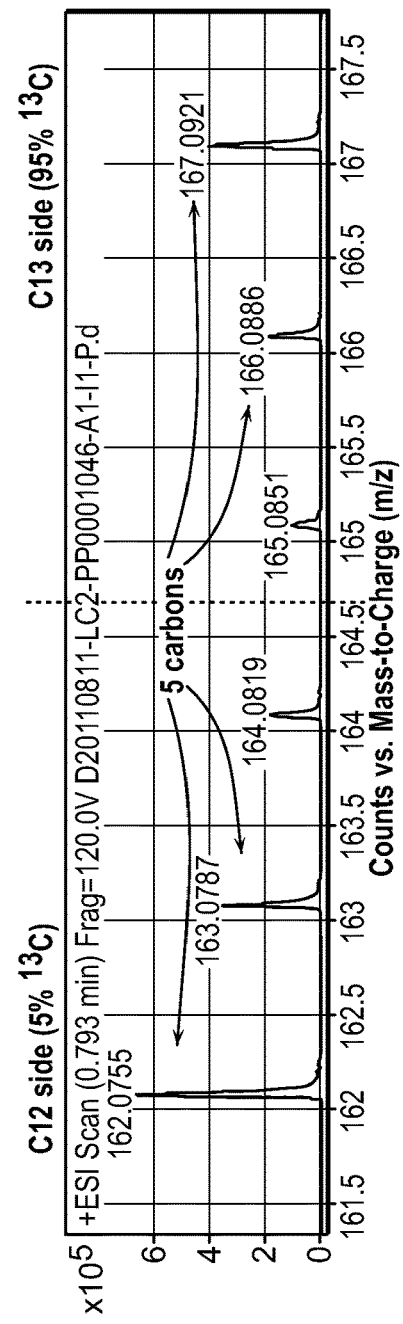

The present disclosure relates to structural elucidation of isotopically labeled analytes using chromatography, mass spectrometry and data-independent acquisition. The present disclosure can be used for rapid screening of analytes, such as the metabolome, including the simultaneous collection of both qualitative and quantitative information of known and unknown analytes.

In one embodiment, the present disclosure relates to a method including receiving a high energy fragmentation mass spectrum and a low energy fragmentation mass spectrum of a ion, identifying at least one characteristic set of peaks in the low energy fragmentation mass spectrum, identifying at least one characteristic set of peaks in the high energy fragmentation mass spectrum that are substantially similar to the characteristic set of peaks in the low energy fragmentation mass spectrum; and determining a chemical structure of the ion from the combination of at least one characteristic set of peaks in the high energy fragmentation mass and the at least one characteristic set of peaks in the low energy fragmentation mass.

The high energy fragmentation mass spectrum and a low energy fragmentation mass spectrum of a ion can be generated using data independent methods, such as $MS^E$. See U.S. Pat. Nos. 6,717,130 and 6,586,727, entire disclosures of both are incorporated by reference herein in their entirety. For example, a voltage can be applied to a fragmentation means to generate the ions. High energy fragmentation can occur by supplying a voltage to a fragmentation means wherein the voltage is greater than or equal to about 15V, 20V, 0.25V, 30V, 50V, 100V, 150V or about 200V. Low energy fragmentation can occur by supplying a voltage to a fragmentation means wherein the voltage is less than or equal to about 10V, 9V, 8V, 7V, 6V, 5V, 4.5V, 4V, 3.5V, 3V, 2.5V, 2V, 1.5V, 1V, 0.5V or about substantially 0V. These sets of values can be used to define a range of high and low energy, such as about 15V to about 25V, and about 5V to about 2.5V. In some embodiments, a voltage between 5V and 15V could be used as the high and low voltages such that a proportion of the ions in the high energy mode would not actually be fragmented and similarly, in the low energy mode, a proportion of the ions would be fragmented.

In one embodiment, a tandem quadrupole orthogonal TOF mass spectrometer can be used in a way in which candidate parent ions are discovered using a method in which sequential low and high collision energy mass spectra are recorded. The switching back and forth is not substantially interrupted. Instead a complete set of data can be acquired which can then be processed afterwards. Fragment ions can be associated with parent ions by closeness of fit of both their respective elution times and their characteristic set of peaks derived from being isotopically labeled in the mass spectrum. The unambiguous assignment of one or more, and in some instances substantially all, of the fragment ions to the parent ion can be confirmed without interrupting the acquisition of data, and information need not be lost.

Once an experimental run has been completed, the high and low energy fragmentation mass spectra can then be post-processed. Parent ions can be recognized by identifying at least one characteristic set of peaks in the low energy fragmentation mass spectrum. Each parent ion can generate a unique set of mass spectrum peaks by virtue of being isotopically labeled. For example, analytes isotopically labeled using IROA can have a unique set of mass spectrum peaks made up of halves each having the mirror image of the other. Daughter ion(s) associated with the parent ion can be recognized by identifying at least one characteristic set of peaks in the high energy fragmentation mass spectrum that are substantially similar to the characteristic set of peaks in the low energy fragmentation mass spectrum. The two sets of peaks can be substantially similar in at least one of the following ways—they can have the same number of peaks, substantially the same spacing between any two or more peaks, substantially the same intensity ratio between any two or more peaks, or combinations thereof. In some embodiments, the two sets of peaks are substantially similar in at least two of these ways. In other embodiments, the two sets of peaks are substantially similar in at least two of these ways wherein one of the ways included the presence of a symmetric or asymmetric mirror image (e.g., isotopic ratio outlier analysis or IROA).

The present disclosure can be used with all methods and testing techniques using isotopically labeled analytes, including IROA. See also Jong et al., Stugg et al., Zhou et al. and Mahieu et al.

The basic IROA protocol is shown in FIG. 1. IROA is a stable isotopic labeling technique that utilizes the creation of distinct signatures in the molecules of a biological sample for identification and quantification. The technique can be used in either an unbiased (untargeted) or targeted metabolic profiling methodology by varying experimental design. The molecular contents of a cell can be labeled by replacing their entire carbon content with a stable isotope, such as the stable $^{13}C$ isotope, centered on at least two different percentage amounts, such as either a 5% or 95% isotopic balance. The at least two different percentage amounts are used to create unique, highly informative isotopic patterns. The use of randomly labeled, uniform isotopic abundance can create characteristic isotopic patterns that can be detected. In some embodiments, the molecular contents of a cell can be labeled by replacing their entire carbon content with a stable isotope, such as the stable $^{13}C$ isotope, centered on at least three or more different percentage amounts, such as either a 5%, 50% and 95% isotopic balance.

One of the benefits of IROA over other stable isotopic labeling techniques is that once the labeling step takes place all biologically derived molecules can be distinguishable from artifacts (which are present at only natural abundance), and each peak has a signature pattern. After the cells are incubated in the appropriate media, they are recombined together. The mass spectral scans from these pooled samples can show the pairing of biological peaks allowing the removal of artifacts and the reinforced identification of the compounds the peaks represent because the distance between the paired peaks exactly corresponds to the number of carbons in the molecule.

For example, a homogeneous cell population can be divided into equal-sized "experimental" and "control" groups. The biological compounds in these groups can be labeled using an isotopically-defined growth media in which all of the carbon components in the experimental and control samples are replaced with randomly and universally enriched 5% or 95% $^{13}C$. After a certain amount of time, e.g., after at least about 5 subsequent cell divisions, the experiment group can be exposed to a stressor (e.g., chemical, genetic, environmental, etc.). In some embodiments of the present disclosure, the experimental group does not require exposure to a stressor. When the experiment has concluded, the experimental sample can be mixed with the control sample and analyzed using mass spectrometry. The admixing of samples increases data quality as sample-to-sample variance is reduced and the identification of all biological compounds is enhanced.

The Basic IROA protocol relies on the creation of isotopic patterns by growing cells on media wherein all the carbon sources contain defined isotopic balances. For instance, where the isotopic balance is 5% $^{13}C$, the pattern for 5 carbon molecule will look like the peaks shown on the C12 side of FIG. 1. The same compound with an isotopic balance of 95% $^{13}C$ will look like its mirror image as shown on the C13 side of FIG. 1. Since non-biologically derived compounds do not have IROA patterns, artifactual peaks may be identified and removed from consideration. These characteristics greatly simplify and strengthen the quality for the interpretation of a mass spectrum of a biological sample.

Figure 2:
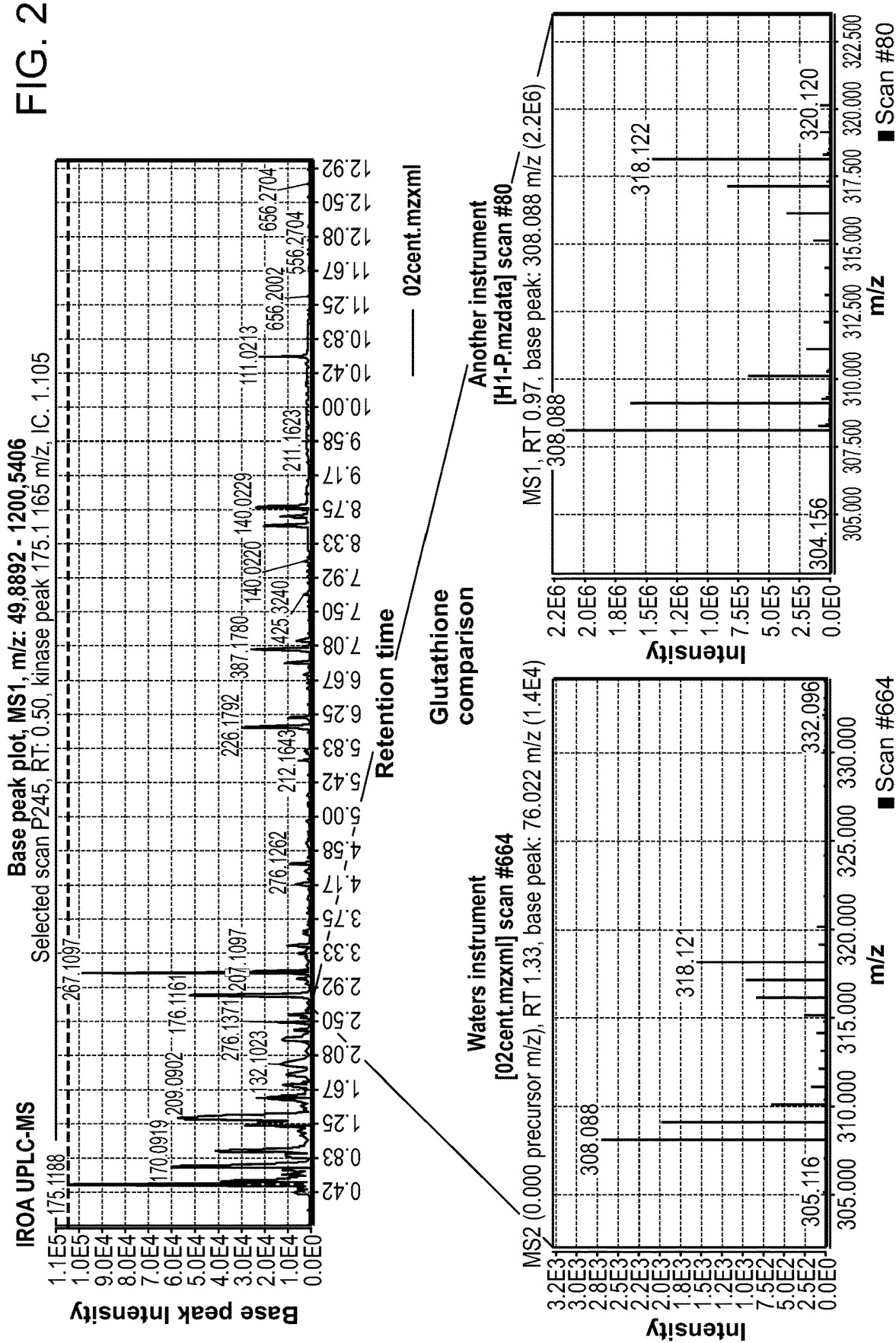
FIG. 2 shows an exemplary chromatogram of a complex sample with co-eluting peaks and a low energy fragmentation mass spectrum of the chromatographic peak containing glutathione from two different mass spectrometers.

In one embodiment, the high and low energy fragmentation mass spectra are generated at substantially the same time in association with real time analysis of ions from the eluent delivered from a chromatography device. FIG. 2 shows a representative chromatogram of a complex sample having many peaks, some co-eluting. The sample was generated using the IROA protocol. A chromatographic peak containing glutathione was analyzed using two different mass spectrometer which generated similar low energy fragmentation mass spectra. The glutathione parent ion has a characteristic peak pattern as shown in FIG. 2. The low energy fragmentation mass spectra can be used to identify daughter ions in an associated high energy fragmentation mass spectra having a substantially similar characteristic peak pattern.

Figure 3:
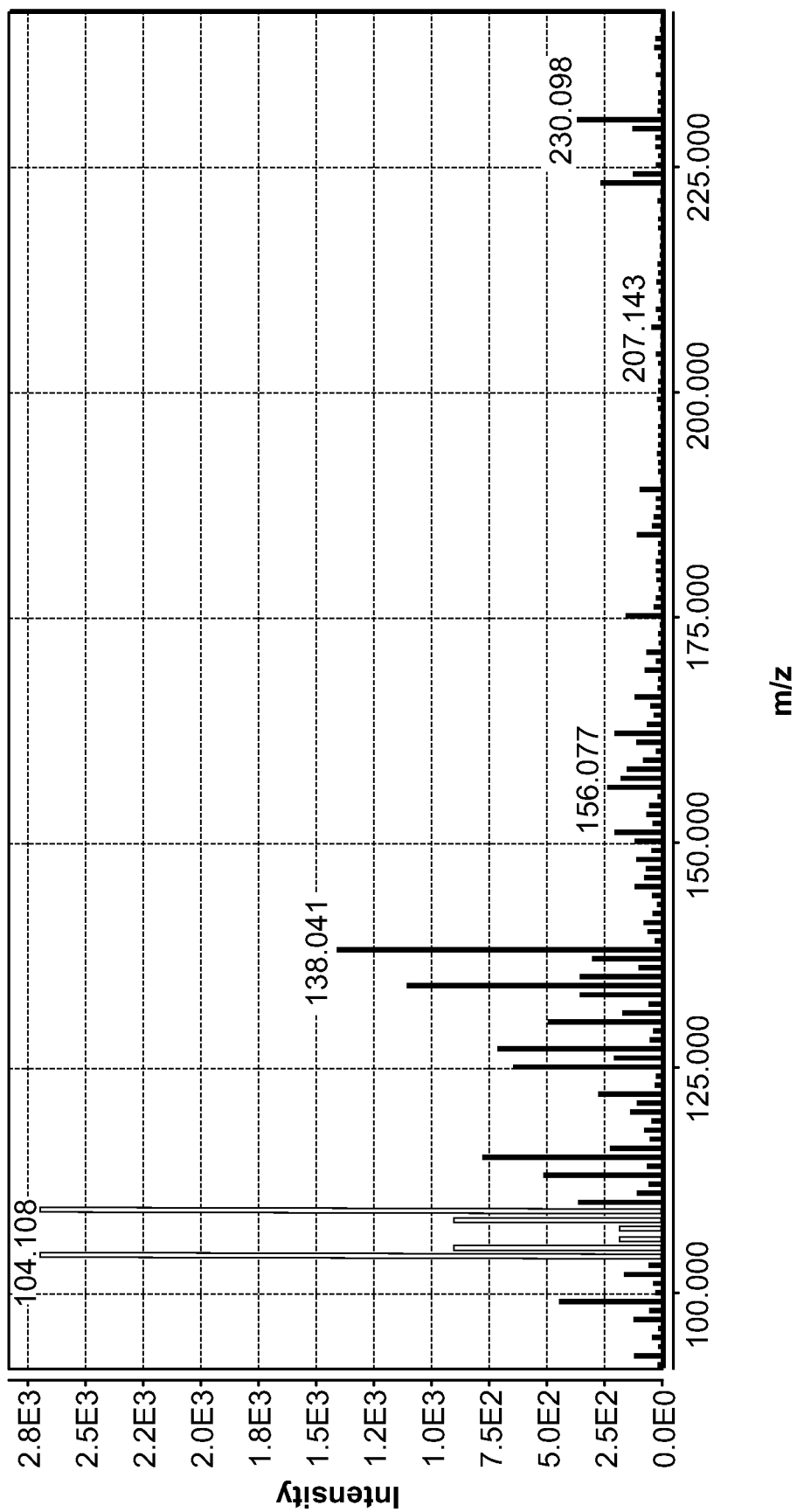
FIG. 3 shows an exemplary high energy fragmentation mass spectrum of the chromatographic peak containing glutathione as shown in FIG. 2.

FIG. 3 shows a high energy fragmentation mass spectrum associated with the low energy fragmentation mass spectra of FIG. 2. The characteristic peak pattern of the parent is identified for a daughter ion as shown in high energy fragmentation mass spectrum (e.g., 104, 108). The daughter peaks can be identified by the similar number of peaks (subject to the signal/noise ratio), the spacing of the peaks, the relative intensity of the peaks to each other, as well as the peak halves having similar mirror images of the other, or combinations thereof.

Figure 4:
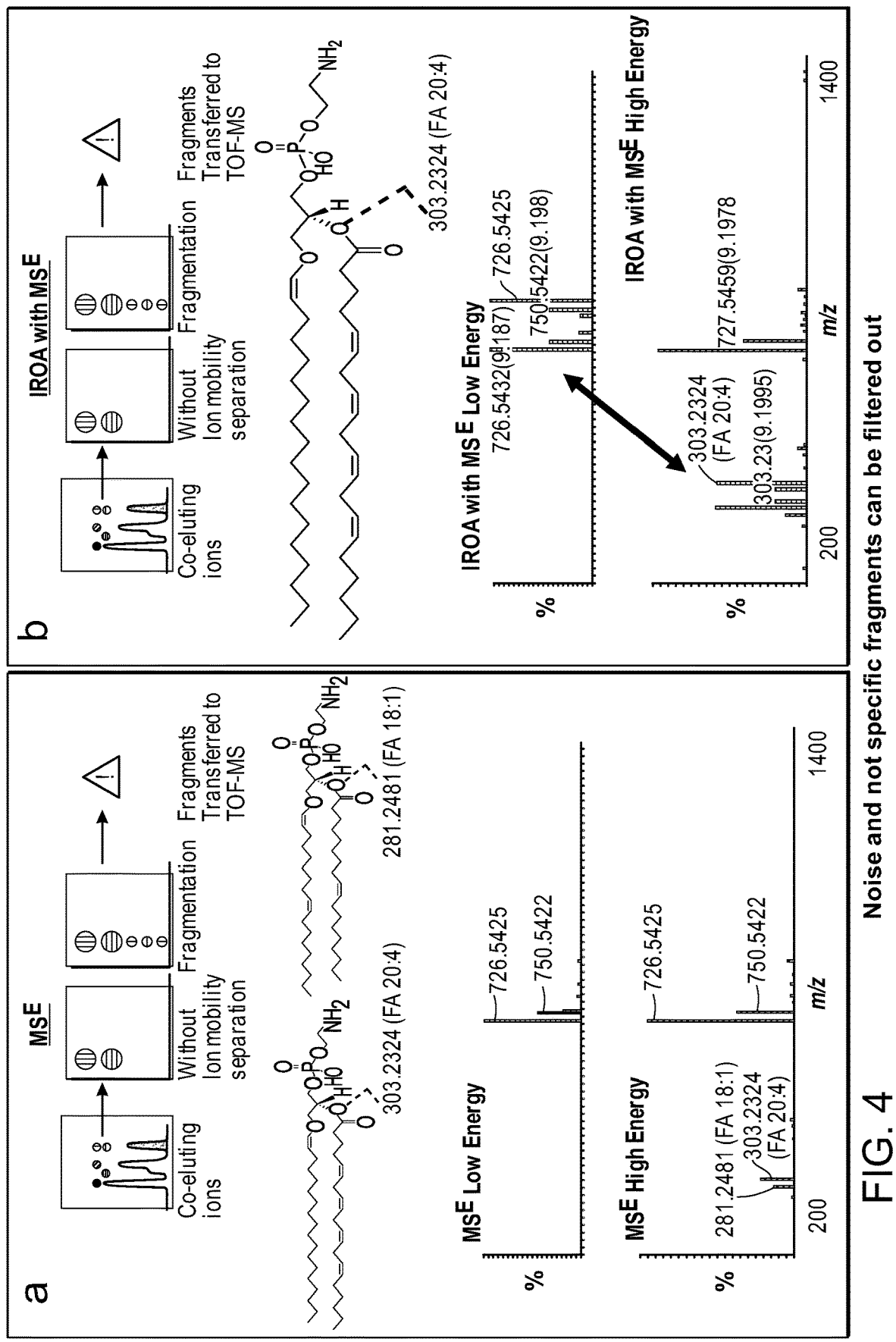
FIG. 4 shows an exemplary comparison of a chromatography, mass spectrometry, data-independent acquisition analysis of a non-isotopically labeled samples (FIG. 4a) and an isotopically labeled sample (FIG. 4b).

By contrast, without isotopic labeling the characteristic set of peaks based on the presence of the isotopically labeled parent and subsequent daughter peaks used to unambiguously identify the parent/daughter peaks are not present. FIG. 4 shows the analysis of co-eluting ions using mass spectrometry with data independent acquisition without isotopical labeling (FIG. 4a) and with isotopic labeling (FIG. 4b). The co-eluting ions, without ion mobility separation, undergo fragmentation and subsequent analysis by TOF-MS. Both low and high energy fragmentation mass spectra are obtained for an analyte of interest. In FIG. 4a, the characteristic set of peaks associated with the isotopically labeled analyte are missing and thus cannot be used to match the parent and the daughter peaks. In FIG. 4b, the characteristic set of peaks associated with the isotopically labeled analyte are present and thus can be used to match the parent and the daughter peaks.

Ion mobility can also be used. Ion mobility separates ions according to their mobilities, e.g., traveling-wave ion mobility spectrometry (IMS) or drift tube IMS (DT IMS). Fragmentation can occur before or after ion mobility separation, either in source or in an appropriate collision cell(s). The rotationally averaged collision cross section (CCS) is a physical property of ions reflecting the shape of the ions can be derived from the times ions taek to cross the ion mobility separation cell (i.e., drift time). Fragment ions separated by drift time can be associated with both unique m/z and CCS values based on the isotopic distribution of the precursor ion which can be used to enhance identification and quantification. Isotopes retain similar CCS values, which can then be used to deconvolute and denoise, allowing the separation of isotopic clusters from other isobaric species.

In another embodiment, two or more co-eluting isotopically analytes can be identified using the methodology of the present disclosure. The co-eluting analytes generate co-eluting ions under fragmentation and subsequent analysis by TOF-MS. Both low and high energy fragmentation mass spectra are obtained for the two or more analytes. A first, second, third, etc. set of characteristic peaks can be identified in the low energy fragmentation mass spectrum associated with each parent ion. Each characteristic set of peaks can be unique to each of the first, second, third, etc. parent ions. Each set can have substantially different numbers of peaks, m/z values, relative spacing of peaks, relative peak intensities, etc.

A first, second, third, etc. set of characteristic peaks can be identified in the high energy fragmentation mass spectrum that can be associated with a respective parent ion of the isotopically labeled analytes. For parent ions having more than one daughter ions, multiple first, multiple second, multiple third, etc. sets of characteristic peaks can be identified in a high energy fragmentation mass spectrum that can be associated with a respective parent ion of the isotopically labeled analytes. Prior the present disclosure, the application of data independent or data dependent acquisition only to these samples lead to MS/MS spectra containing a mixture of fragments deriving from multiple co-eluting or co-isolated precursors which complicated the interpretation of spectra. The present disclosure clarifies the interpretation by allowing unambiguous matching of one or more parent ions and one or more daughter(s) peaks which facilitates structural elucidation of individual analytes in complex samples.

Once the daughter ion(s) associated with the parent ion are identified, a chemical structure of the parent ion (or analyte of interest) can be determined from the combination of at least one characteristic set of peaks in the high energy fragmentation mass and the at least one characteristic set of peaks in the low energy fragmentation mass. The determination can be performed or assisted with a data processing method or software tool for processing the mass spectra of associated (e.g., chronologically similar) high and low energy fragmentation mass spectra. The method or tool can explore the mass spectral features unique to the isotopically labeled analyte, ion, fragment, parent/daughter, etc. These features can include peak pairs having fixed mass differences, relative intensity ratios, etc. The common unique feature(s) among the spectra can be identified and used to determine the family of mass spectra peaks associated with any one analyte and allow the structure of that analyte to be elucidated.

The present disclosure can be used for the analysis of stable isotopes generated by a variety of methodologies. The term "stable isotopes" means an isotope of a compound having identical numbers of protons and electrons, but having one or more additional neutron, which increases the molecular weight of the compound by essentially one or more mass units. See, e.g., U.S. Pat. No. 7,820,964; U.S. 2003/0180710; U.S. 2008/0050833; and U.S. 2012/0165227, the disclosures of each is incorporated by reference in their entirety. For example, the present disclosure can be used for targeted analyses, such as the incorporation of a specific labeled atom into other specific molecules. The present disclosure can also be used in connection with internal standards for their non-labeled counterparts.

As described in U.S. 2012/0165227, for example, stable isotopes of carboxylic acids in the biological samples, e.g., metabolome, can be generated by converting to a labeled ester by reaction with an isotopically substituted aromatic compound. Similarly, as described in U.S. 2008/0050833, for example, stable isotopes of amines can be generated by reaction with a labeled methylacetimidate, and carboxylic acids can be generated by reaction with a labeled formaldehyde or cholamine.

After chromatographic separation and introduction into the mass spectrometer, the precursor can be fragmented (e.g., low energy, high energy, etc.) and can appear as a related set of ions. The different ions in the set correspond to different isotopic compositions and charges of the common precursor. Each ion within the related set of ions can produce a characteristic peak or set of peaks related by retention time and peak shape. Since these ions originate from a common precursor, the peak retention time and peak shape of each ion or set of ions is related, if not identical within some measurement tolerance. The MS acquisition of each precursor can produce multiple ion detections for all isotopes and charge states, all sharing substantially the same peak retention-time and peak shape. Deconvolution of these clusters of ions, at multiple charge states, can be performed to indicate the presence of one or more single precursors each having a unique monoisotopic mass, at a specific retention time, of a measured signal intensity, in a charge state.

The data processing and/or deconvolution can be implemented by computer software executing on a computer. The software can be configured to perform a number of tasks, including providing visual displays of the spectra and/or chromatograms as well as providing tools for performing mathematical analysis on the data. The analyses provided by the software can include analyzing the results obtained from a single injection and/or the results obtained from a set of injections to be viewed and further analyzed.

The present disclosure is applicable to any sample, e.g., a complex biological sample, that can be isotopically labeled. For example, the present disclosure can be used to analyze the metabolome. The metabolome is the complete set of small-molecule chemicals found within a biological sample. The biological sample can be a cell, a cellular organelle, an organ, a tissue, a tissue extract, a biofluid or an entire organism. The small molecule chemicals found in a given metabolome can include both endogenous metabolites that are naturally produced by an organism (such as amino acids, organic acids, nucleic acids, fatty acids, amines, sugars, vitamins, co-factors, pigments, antibiotics, etc.) as well as exogenous chemicals (such as drugs, environmental contaminants, food additives, toxins and other xenobiotics) that are not naturally produced by an organism. In some embodiments, a metabolite can be a small molecule having a molecular weight of less than about 1500 Daltons. For example, glycolipids, polysaccharides, short peptides (<14 amino acids) and small oligonucleotides (<5 bases) can be metabolites.

The present disclosure can be used for fluxomics, or the analyze of metabolic reaction rates in a biological system (e.g., flux analysis). In general, fluxomics refers to inferring or predicting the rates of metabolic reactions in biological systems, including the rate that molecules move through a metabolic pathway. The total set of fluxes in a metabolic network is the fluxome. The methodology described herein can follow the metabolic fate of one or more labeled precursor ions (e.g., $^{13}C$ glucose) as they undergo various metabolic reactions. As described in U.S. 2003/0180710, for example, the labeled precursor ions can be one or more compounds that are involved in one or more cellular metabolism functions. The changing pattern of distribution of these ions, e.g., $^{13}C$ glucose, in intercellular metabolic intermediates can identify and provide a measure of metabolic reactions and rates.

In another embodiment, the present disclosure relates to a method of analyzing at least two ions in a sample. For example, the method can include receiving a high energy fragmentation mass spectrum and a low energy fragmentation mass spectrum of at least two ions, identifying at least one characteristic set of peaks in the low energy fragmentation mass spectrum for each ion, identifying at least one characteristic set of peaks in the high energy fragmentation mass spectrum for each ion that are substantially similar to the characteristic set of peaks in the low energy fragmentation mass spectrum for each ion, and determining a chemical structure of each ion from the combination of at least one characteristic set of peaks in the high fragmentation mass and the at least one characteristic set of peaks in the low energy fragmentation mass for each ion.

In another embodiment, the present disclosure relates to a method including providing an ion source for generating ions, passing said ions to a fragmentation means including a collision cell, operating said fragmentation means in a first mode wherein at least a portion of said ions are fragmented to produce daughter ions, recording a mass spectrum of ions emerging from said fragmentation means operating in said first mode as a high energy fragmentation mass spectrum, switching said fragmentation means to operate in a second mode wherein substantially fewer ions are fragmented, recording a mass spectrum of ions emerging from said fragmentation means operating in said second mode as a low energy fragmentation mass spectrum, repeating these steps a plurality of times, identifying at least one characteristic set of peaks in the low energy fragmentation mass spectrum, identifying at least one characteristic set of peaks in the high energy fragmentation mass spectrum that is substantially similar to the characteristic set of peaks in the low energy fragmentation mass spectrum, and determining a chemical structure associated with the at least one characteristic set of peaks in the high energy fragmentation mass and the at least one characteristic set of peaks in the low energy fragmentation mass. See U.S. Pat. Nos. 6,717,130 and 6,586,727, incorporated by reference in their entirety above, for, but not limited to, a more detailed disclosure the data-independent acquisition equipment, conditions and methodology.

The ion source may be either an electrospray, atmospheric pressure chemical ionization or matrix assisted laser desorption ionization ("MALDI") ion source. The ion source can also be an ambient ionization technique, including atmospheric solid analysis probe (i.e., ASAP), direct analysis in real time (DART®, Joel USA, Inc.), rapid evaporative ionization mass spectrometry (REIMS), desorption electrospray ionization (DESI), or nanostructure initiated mass spectrometry (NIMS).

Direct Analysis in Real Time is an atmospheric pressure ion source that can instantaneously ionize gases, liquids or solids in open air under ambient conditions. It is an ambient ionization technique that does not require sample preparation, so materials can be analyzed by mass spectrometry in their native state. Ionization can take place directly on the sample surface. Liquids can be analyzed by, for example, dipping an object (such as a glass rod) into the liquid sample and then presenting it to the DART® ion source. Vapors can be introduced directly into the DART® gas stream.

Atmospheric Solids Analysis Probe is an atmospheric pressure ion source that can directly analyze samples using an atmospheric pressure ionization (API) source. The ASAP probe can analyze solid, liquid, tissue, or material samples. In ASAP, vaporization of a sample can occur when it is exposed to a hot desolvation gas, e.g., nitrogen, from an probe, e.g., an electrospray ionization or atmospheric pressure chemical ionization probe.

Rapid Evaporative Ionization Mass Spectrometry (REIMS) is an ionization technique that can be used as a source for direct analysis of samples by mass spectrometry. REIMS is an atmospheric pressure ion source that can ionize gases, liquids or solids in open air under ambient conditions. The REIMS ionization source can be a probe that can be used to remotely test the samples. See U.S. Patent Publication No. 2012/0156712, the disclosure of which is incorporated herein in its entirety.

Desorption electrospray ionization (DESI) is an ambient ionization technique that can be used in mass spectrometry for chemical analysis. It is an atmospheric pressure ion source that ionizes gases, liquids and solids in open air under ambient conditions. DESI is a combination of electrospray (ESI) and desorption (DI) ionization methods. Ionization can take place by directing an electrically charged mist to a sample surface. The electrospray mist can be attracted to the surface by applying a voltage on the sample or sample holder. After ionization, the ions can travel through air into the atmospheric pressure interface which can be connected to a mass spectrometer.

Such ion sources may be provided with an eluent over a period of time, the eluent having been separated from a mixture by means of liquid chromatography or capillary electrophoresis. The present disclosure can also be used with atmospheric pressure gas chromatography, carbon dioxide based chromatography and supercritical fluid chromatography, as well as ion mobility spectrometry (e.g., IMS, GC-IMS, LC-ISM) such as in a high definition $MS^E$ acquisition method.

In a particular embodiment, the present disclosure includes a chromatographic system for performing a separation coupled to a mass spectrometer capable of data independent acquisition (e.g., the generation of related low and high energy fragmentation spectra) that allows retention time alignment of a parent spectra with a fragment spectra.

The disclosures of all cited references including publications, patents, and patent applications are expressly incorporated herein by reference in their entirety.

When an amount, concentration, or other value or parameter is given as either a range, preferred range, or a list of upper preferable values and lower preferable values, this is to be understood as specifically disclosing all ranges formed from any pair of any upper range limit or preferred value and any lower range limit or preferred value, regardless of whether ranges are separately disclosed. Where a range of numerical values is recited herein, unless otherwise stated, the range is intended to include the endpoints thereof, and all integers and fractions within the range. It is not intended that the scope of the invention be limited to the specific values recited when defining a range.

The present invention is further defined in the following Examples. It should be understood that these Examples, while indicating preferred embodiments of the invention, are given by way of illustration only.

EXAMPLES

Example 1—Structural Elucidation of a Metabolome Using Isotopic Ratio Outlier Analysis (IROA) in Combination with UHPLC-QTOF and Data-Independent Acquisition Metabolite identification represents a bottleneck of most metabolomics studies. This can be aggravated by the presence of noise signals, impurities due to sample collection and extraction procedures and other non-biological relevant information. Isotopic Ratio Outlier Analysis (IROA) protocol can mitigate several of these commonly encountered sources of variance by using specific isotopic signature (FIG. 1). Once the biological relevant analytes have been identified, the characterization of their structure often relies only on accurate mass and isotopic pattern. The combination of IROA and UHPLC-QTOF with data-independent acquisition was used for the rapid screening of yeast cells. Both qualitative and quantitative information was simultaneously collected for known and unknown metabolites.

In one analysis, hydrophobic metabolites, e.g., lipids (including anthranilic acid), were separated using an ACQUITY UPLC® system (Waters Corporation, Milford, Mass., USA) equipped with a CSH C18 column (2.1×100 mm ID, 1.7 μm). A gradient elution was performed. Mobile phase A was composed of 60:40 (v/v) 10 mM ammonium formate in acetonitrile/water. Mobile phase B was composed of 10 mM formate in isopropanol/acetonitrile. The elution gradient was as follows: 0-2 min, 40-43% B; 2.0-2.1 min, 43-50% B; 2.1-12 min, 50-54% B; 12-12.1 min, 54-70% B; 12.1-18 min, 70-99% B; 18-18.1 min, 99-40% B; 18.1-20 min, 40% B. The column was kept at 55° C. The flow rate was 0.4 mL/min and the injection volume was 5 μL.

In another analysis, polar metabolites were separated using an ACQUITY UPLC® system (Waters Corporation, Milford, Mass., USA) fitted with a BEH HILIC column (2.1×100 (or 150) mm ID, 1.7 μm). Mobile phase A was composed of 95:5 acetonitrile/water (v/v) containing 10 mM ammonium acetate (pH 8.0). Mobile phase B was composed of 50:50 acetonitrile/water (v/v) containing 10 mM ammonium acetate (pH 8.0). A 10-minute linear gradient, from 100% to 80% A, with a 3-minute re-equilibration time, was applied. The column was kept at 30° C. The flow rate was 0.5 mL/min and the injection volume was 5 μL.

MS analyses were performed on an ion-mobility-enabled quadrupole, time-of-flight (QTOF) mass spectrometer (Synapt® G2-S, Waters Corporation, Milford, Mass., USA). Data were acquired, from 50 m/z to 1,500 m/z in both positive and negative electrospray ionization modes. The mass spectrometer was operated under the following conditions: capillary voltage 2.0 KV (+ve) and 1.0 KV (−ve); cone voltage 30 V; transfer CE ramp 20 to 50 V; source temperature 120° C.; desolvation temperature 550° C.; cone gas 50 L/h; MS gas nitrogen. Data were collected in two channels: low collision energy (6.0 V), for the molecular ions, and high collision energy (15-40 V), for product ions. When activated, the ion-mobility gas was nitrogen, and the T-wave velocity and height were 900 m/s and 40 V, respectively.

Pooling together the cells grown in 95% and 5% $^{13}C$ media allowed all artifacts (compounds not of biological origin) to be recognized as such (by their absence of isotopic signatures) and discounted or removed.

The QTOF was operated in DIA mode. The operation of the mass spectrometer in data independent mode utilized alternating low and elevated collision energy, independently from the previous scan, with no pre-selection of precursor ions by the quadrupole mass analyzer. Low collision-energy acquisition generates information about the intact precursor ions. Elevated collision energy provides information about fragments.

The high and low energy fragmentation mass spectra were then processed. The number of carbons in each isotopic peak and accurate masses were used to determine the molecular formula of each metabolite with high confidence. Peaks of biological origin were perfectly paired: each isotopic envelope is half control and half experimental. The ratio of (95% $^{13}C$/5% $^{13}C$) paired peaks can be used to determine which metabolic pools are affected by treatments. Molecular formulae were calculated to provide tentative identification for previously unknown metabolites (FIG. 2). Fragment spectra were manually extracted and matched with precursor based on their characteristic isotopic patterns (FIG. 3).

Select parent ions were identified as each having a characteristic set of isotopic peaks in the low energy fragmentation mass spectrum. The characteristic set of isotopic peaks are associate with the isotopic content. These peaks can be characterized by the number of peaks, their m/z value, the spacing or difference in m/z between any two or more peaks, and the ratio of intensities between any two or more peaks. In some embodiments, the set of isotopic peaks can be made up of two halves each having the mirror image of the other. The mirror images can be symmetric (e.g., IROA without a stressor) or can be asymmetric, e.g. wherein one mirror image has a uniformly reduced intensity (e.g., IROA with a stressor). In other embodiments, the set of isotopic peaks do not have a mirror image (e.g., non-IROA isotopic techniques). It has been discovered that the same characteristic set of isotopic peaks associated with the parent ion in the low energy fragmentation mass spectrum also exists for the daughter ions in the high energy fragmentation mass spectrum. Combinations of parent-daughter(s) ions, and related daughter ions, were recognized and identified by comparing the high energy fragmentation mass spectrum with the low energy fragmentation mass spectrum obtained at the substantially the same time. Here, the peaks of biological origin were perfectly paired in that each IROA envelope is half control and half experimental. These combinations were used to determine the molecular formula of each metabolite with high confidence.

For embodiments where one of the isotope groups, i.e., 95% $^{13}C$ or 5% $^{13}C$, were stressed or treated, the ratio of paired peaks can be used to determine which metabolic pools are affected by the stress or treatments.

Figure 5:
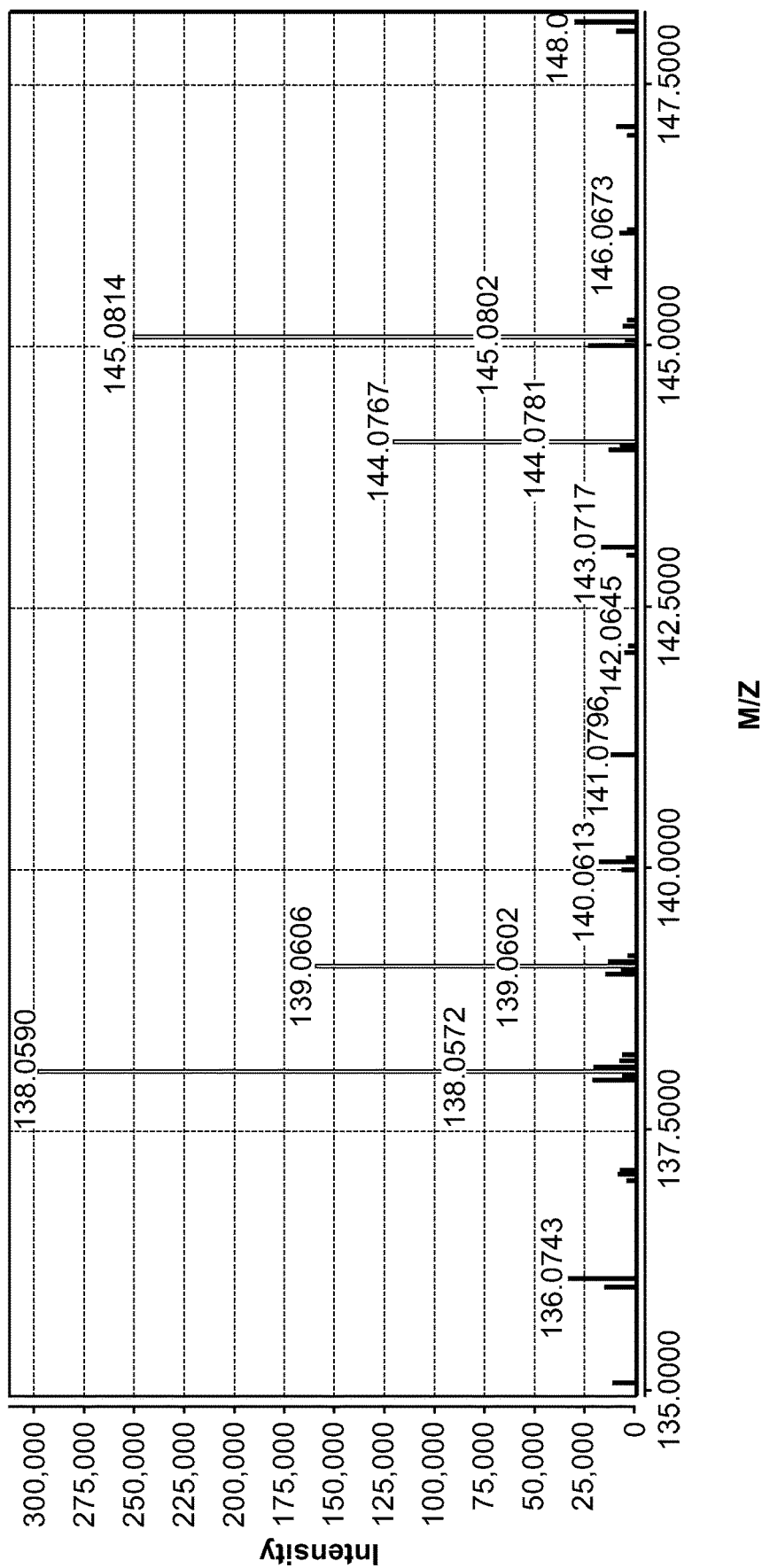
FIG. 5 shows the identification of isotopically labelled anthranilic acid using UPLC separation following ESI and data-independent acquisition with ion mobility in a TOF instrument.

Metabolites were tentatively identified and compared against libraries of compounds for their characteristic isotopic pattern, e.g., $^{12}C$ base peak, $^{12}C$ $M^{+1}$, $^{13}C$ base peak, $^{13}C$ $M^{-1}$, and fragment peaks and intervening peaks. FIG. 5 shows the representative identification of anthranilic acid following UHPLC-DIA-MS analysis.

Using the methodology of the present disclosure, the molecular formulae of previously unknown metabolites was calculated to provide tentative identification. The use of the data-independent acquisition mode with the UHPLC-DIA-MS system allowed for simultaneous acquisition of accurate mass measurement of precursor ions (from the low energy collision energy data) and fragment ions (from the ramping elevated collision energy data) in a single analytical run for virtually all detectable ions in a single analytical run (without need to rerun the sample or perform a data-dependent acquisition). Fragment ions were subsequently matched by recognizing the same characteristic set of isotopic peaks with the appropriate precursor ions using retention time correlation. Using this approach, the exact formula for each IROA fragment was assigned, which facilitated the structure elucidation of unknown metabolites.

As is demonstrated by the above example, the characteristic set of peaks allows for the unambiguous assignment of one or more, and in some instances substantially all, of the daughter peak(s) to the true parent. This unambiguous assignment cannot be performed in any other way. Using the methodology of the present disclosure, such as the combination of IROA and UHPLC-QTOF with DIA, an in depth description of complex samples, such as the metabolome, can be obtained.

While this disclosure has been particularly shown and described with reference to example embodiments thereof, it will be understood by those skilled in the art that various changes in form and details may be made therein without departing from the scope of the invention encompassed by the appended claims.

I claim:

1. A method of analyzing a biological sample, the method comprising:
   (a) isotopically labeling metabolites in the biological sample;
   (b) separating the isotopically labeled metabolites using chromatography;
   (c) generating a low energy fragmentation mass spectrum of parent ions of the isotopically labeled metabolites and generating a high energy fragmentation mass spectrum of fragment ions of the parent ions, each mass spectrum generated using a mass spectrometer operating in data independent mode;
   (d) identifying at least one characteristic set of peaks in the low energy fragmentation mass spectrum corresponding to the parent ions of the isotopically labeled metabolites;
   (e) identifying at least one characteristic set of peaks in the high energy fragmentation mass spectrum that are substantially similar to the characteristic set of peaks in the low energy fragmentation mass spectrum and correspond to the fragment ions of the parent ions; and
   (f) determining a chemical structure of the ions of the isotopically labeled metabolites from the combination of at least one characteristic set of peaks in the high fragmentation mass corresponding to the fragment ions of the parent ions and the at least one characteristic set of peaks in the low energy fragmentation mass corresponding to the parent ions of the isotopically labeled metabolites.

2. The method of claim 1, wherein the high energy fragmentation mass spectrum and the low energy fragmentation mass spectrum are generated using a time of flight mass spectrometer.

3. The method of claim 1, wherein the high energy fragmentation mass spectrum and the low energy fragmentation mass spectrum are generated at substantially the same time.

4. The method of claim 1, wherein the characteristic set of peaks in the high energy fragmentation mass spectrum has substantially the same number of peaks, substantially the same spacing between any two or more peaks, or substantially the same intensity ratio between any two or more peaks as the characteristic set of peaks in the low energy fragmentation mass spectrum.

5. A method of analyzing a biological sample, the method comprising:
   (a) isotopically labeling metabolites in the biological sample;
   (b) separating the isotopically labeled metabolites using chromatography;
   (c) providing an ion source for generating ions of the isotopically labeled metabolites;
   (d) passing said ions of the isotopically labeled metabolites to a fragmentation means including a collision cell;
   (e) operating said fragmentation means in a high energy mode wherein at least a portion of said ions of the isotopically labeled metabolites are fragmented to produce daughter ions;
   (f) generating a mass spectrum of ions emerging from the fragmentation means operating in the high energy mode as a high energy fragmentation mass spectrum, the mass spectrum generated using a mass spectrometer operating in data independent mode;
   (g) switching the fragmentation means to operate in a low energy mode wherein substantially fewer ions of the isotopically labeled metabolites are fragmented;
   (h) generating a mass spectrum of ions emerging from the fragmentation means operating in the low energy mode as a low energy fragmentation mass spectrum;
   (i) repeating steps (e)-(h) a plurality of times;
   (j) identifying at least one characteristic set of peaks in the low energy fragmentation mass spectrum, the mass spectrum generated using a mass spectrometer operating in data independent mode;
   (k) identifying at least one characteristic set of peaks in the high energy fragmentation mass spectrum that is substantially similar to the characteristic set of peaks in the low energy fragmentation mass spectrum;
   (l) determining a chemical structure associated with the at least one characteristic set of peaks in the high energy fragmentation mass spectrum and the at least one characteristic set of peaks in the low energy fragmentation mass spectrum.

6. The method of claim 5, wherein the ion source is selected from the group consisting of electrospray, atmospheric pressure chemical ionization, matrix assisted laser desorption ionization, atmospheric solid analysis probe, direct analysis in real time, rapid evaporative ionization mass spectrometry, desorption electrospray ionization, and nanostructure initiated mass spectrometry.

7. The method of claim 5, wherein the characteristic set of peaks in the high energy fragmentation mass spectrum has substantially the same number of peaks, substantially the same intensity ratio between any two or more peaks as the characteristic set of peaks in the low energy fragmentation mass spectrum.

8. The method of claim 1, wherein the isotopically labeled metabolites are separated using liquid chromatography.

9. The method of claim 5, wherein the isotopically labeled metabolites are separated using liquid chromatography.

10. The method of claim 1, wherein the metabolites in the samples are isotopically labeled using isotopic ratio outlier analysis protocol.

11. The method of claim 5, wherein the metabolites in the samples are isotopically labeled using isotopic ratio outlier analysis protocol.

12. The method of claim 1, wherein the isotopically labeled metabolites in the sample co-elute.

13. The method of claim 5, wherein the isotopically labeled metabolites in the sample co-elute.

* * * * *